United States Patent
Reiner et al.

(10) Patent No.: US 8,927,604 B2
(45) Date of Patent: *Jan. 6, 2015

(54) DICLOFENAC FORMULATIONS AND METHODS OF USE

(71) Applicant: APR Applied Pharma Research s.a., Balerna (CH)

(72) Inventors: Giorgio Reiner, Como (IT); Alberto Reiner, Como (IT)

(73) Assignee: APR Applied Pharma Research s.a., Balerna (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/742,871

(22) Filed: Jan. 16, 2013

(65) Prior Publication Data

US 2013/0245122 A1 Sep. 19, 2013

Related U.S. Application Data

(63) Continuation of application No. 12/399,175, filed on Mar. 6, 2009, now abandoned, which is a continuation of application No. 11/455,120, filed on Jun. 16, 2006, now Pat. No. 7,759,394.

(60) Provisional application No. 60/692,024, filed on Jun. 17, 2005, provisional application No. 60/691,757, filed on Jun. 17, 2005.

(51) Int. Cl.
| | | |
|---|---|---|
| *C07C 229/00* | (2006.01) | |
| *A01N 37/00* | (2006.01) | |
| *A61K 31/185* | (2006.01) | |
| *A61K 31/19* | (2006.01) | |
| *A61K 9/00* | (2006.01) | |
| *A61K 9/08* | (2006.01) | |
| *A61K 31/196* | (2006.01) | |
| *A61K 47/10* | (2006.01) | |

(52) U.S. Cl.
CPC ............ *A61K 31/196* (2013.01); *A61K 9/0095* (2013.01); *A61K 9/08* (2013.01); *A61K 47/10* (2013.01)
USPC .............. 514/553; 514/557; 514/576; 560/47

(58) Field of Classification Search
CPC ... A61K 31/196; A61K 9/0095; A61K 47/10; A61K 9/08
See application file for complete search history.

(56) References Cited

U.S. PATENT DOCUMENTS

| | | | |
|---|---|---|---|
| 3,558,690 A | | 1/1971 | Sallmann et al. |
| 4,689,218 A | | 8/1987 | Gazzaniga et al. |
| 5,458,879 A | * | 10/1995 | Singh et al. .................. 424/400 |
| 6,974,595 B1 | * | 12/2005 | Reiner et al. ................. 424/722 |
| 7,482,377 B2 | * | 1/2009 | Reiner et al. ................. 514/553 |
| 7,687,542 B2 | * | 3/2010 | Reiner et al. ................. 514/553 |
| 7,700,125 B2 | * | 4/2010 | Reiner et al. ................. 424/412 |
| 7,759,394 B2 | * | 7/2010 | Reiner et al. ................. 514/553 |
| 7,939,561 B2 | * | 5/2011 | Schellenger et al. ......... 514/553 |
| 8,097,651 B2 | * | 1/2012 | Reiner et al. ................. 514/553 |
| 2005/0214363 A1 | | 9/2005 | Reiner et al. |
| 2005/0215643 A1 | | 9/2005 | Reiner et al. |
| 2006/0013896 A1 | | 1/2006 | Reiner et al. |

FOREIGN PATENT DOCUMENTS

| | | |
|---|---|---|
| CA | 2131515 | 3/1995 |
| EP | 0418043 | 3/1991 |
| EP | 0466650 | 1/1992 |
| GB | A2401547 | 11/2004 |
| WO | 9403160 | 2/1994 |
| WO | 9614839 | 5/1996 |
| WO | 9744023 | 11/1997 |

OTHER PUBLICATIONS

Gennaro et al. (eds.), Remington's Pharmaceutical Science, 18th Edition, Mack Publishing Co., Easton, PA, 1990, only pp. 1110, 1111, 1637, 1846 and 1847 supplied.*
Gennaro et al. (eds.), "Pharmaceutical Necessities," Chapter 66 in Remington's Pharmaceutical Science, 18th Edition, Mack Publishing Co., Easton, PA, 1990: see in particular col. 2 of p. 1292 wherein "mannitol," and many other "Vehicles" commonly found as components in pharmaceutical compositions, are listed in Table I.*
Gennaro et al. (eds.), Remington's Pharmaceutical Science, 18th Edition, Mack Publishing Co., Easton, PA, 1990, only pp. 386-388 supplied.*
O'Neil et al. (eds.), The Merck Index, An Encyclopedia of Chemicals, Drugs, and Biologicals, 13th Edition, 2001, Merck & Co., Whitehouse Station, NJ, only p. 175 supplied, see entry entries 1024 (Behenic acid).*
Henry, D., et al; "Variability in risk of gastrointestinal complications with individual non-steroidal anti-inflammatory drugs; results of a collaborative meta-analysis"; BMJ; vol. 312, pp. 1563-1566, (1996).
Walker A.M.; "Quantitative studies of the risk of serious hepatic injury in persons being non-steroidal anti-inflammatory drugs"; Arthritis and Rheumatism. vol. 40, No. 2, pp. 201-108 (1997).
Gutthann, S.P., et al; "Non-steroidal anti-inflammatory drugs and the risk of hospitalization for acute renal failure"; Arch. Intern. Med., vol. 156, pp. 2433-2439, (1996).
Amidon, G.L., et al; "A theoretical basis for a biopharmaceutic drug classification: The correlation of in vitro drug product dissolution and in vivi bioavailability"; Ph arm. Research, vol. 12, No. 3, pp. 413-420 (1995).
Neuvonen, P.J., "The effect of magnesium hydroxide on the oral absorption of ibuprofen, ketoprofen and diclofenac"; Br. J. Clin. Pharmac. vol. 31, pp. 263-266, (1991).
Neuvonen, P.J., et al; "Enhancement of drug absorption by antacids"; Clin. Pharmacokinet. 27 (2): pp. 120-128, (1994).
Neuvonen, P.J., et al; "Effect of magnesium hydroxide on the absorption of tolfenamic and mefenamic acids"; Eur. J. Clin. Pharmacol, 35: pp. 495-501, (1988).

(Continued)

*Primary Examiner* — Lawrence E Crane
(74) *Attorney, Agent, or Firm* — Clark G. Sullivan; Troutman Sanders LLP

(57) ABSTRACT

Methods and formulations are provided for treating migraine and other acute pain episodes using diclofenac, and formulations of diclofenac that provide both rapid and sustained relief from acute pain. Methods and formulations are also provided for treating symptoms that often accompany migraine and acute pain such as photophobia, phonophobia, nausea and vomiting.

40 Claims, 1 Drawing Sheet

(56) References Cited

OTHER PUBLICATIONS

Derendorf, H., et al; "Pharmacokinetics of diclofenac sodium after intramuscular administration in combination with triamcinolone acetate"; Eur. J. Clin. Phamacol., 31:363-365 (1986).

Terhaag, B., et. al.; "Bioavailability of a new effervescent tablet diclofenac"; Int. J. Clin., Pharmacol. Ther., 38:546-551 (2000).

Lotsch, J., et al; "Population pharmacokinetics of fast release oral diclofenac in healthy volunteers: relation to pharmacodynamics in an experimental pain model"; Pharmaceutical Research, vol. 17, No. 1, pp. 77-84 (2000).

Marzo, A., et al; "Pharmacokinetics of Didofenac after oral administration of its potassium salt in sachet an tabled formulations"; Arzneim. Forsch., 50:43-47 (2000).

Reiner, V., et al; "Increased absorption rate of diclofenac from fast acting fomulations containing its potassium salt"; Arzneim. Forsch., 51:885-890 (2001).

Fourtillan, J.B. et al; "Etude pharmacocinetique du piroxicam chez l'homme sain"; Therapie, vol. 38, pp. 163-170, (1983).

Brogden, RN., et al; "Diclofenac sodium: A review of its pharmacological properties and therapeutic use in rheumatic diseases and pain of varying origin"; Drugs, 20: pp. 24-48, (1980).

Macia, MA, et al; "Comparative bioavailability of a dispersible formulation of diclofenac and finding of double plasma peaks"; Int. J. Clin. Pharmacol. Ther., 33:333-339 (1995).

Bettini, R., et. al; "Swelling force development as a result of hydrate formation in diclofenac sodium or nitrofurantoin tablets"; S.T.P. Pharma Sciences 10 (4) pp. 335-339, (2000).

Henrikson, P A, et al; Absorption and effect of diclofenac sodium after surgical removal of a lower wisdom tooth; Curr. Ther. Res., 31:30-36 (1982).

Degen, P.H., et al; Pharmacokinetics of diclofenac and five metabolites after single doses in healthy volunteers and after repeated doses in patients; Xenobiotica, 18:1449-1455 (1988).

Maggi, C.A., et al; "Comparative bioavailability of diclofenac hydroxyethylpyrrolidine vs diclofenac sodium in man"; Eur. J. Clin. Pharmacol., 38:207-208 (1990).

Mendes, G.B.B., et al; "Comparative bioavailability of two suspension formulations of potassium diclofenac in healthy male volunteers"; Int. J. Clin. Pharmacol. Thr., 32:131-135 (1994).

Crook, P.R., et al; "The pharmacokinetics of diclofenac sodium in patients with active rheumatoid disease"; Eur. J. Clin Pharmacol., 21:331-334 (1982).

Willis, J.V., et al; "The pharmacokinetics of diclofenac sodium following intravenous and oral administration"; Eur. J. Clin. Phamacol., 16:405-410 (1979).

Willis, J.V., et al; "The influence of food on the absorption of diclofenac after single and multiple oral doses"; Eur. J. Clin. Pharmacol., 19:33-37 (1981).

Reiss, W., et al; "Pharmacokinetics and metabolism of the anti-inflammatory agent Voltaren" Scand. J. Reumatol., Suppl. 22:17-29 (1978).

Physicians' Desk reference; Novartis Pharmaceutical Corp., pp. 1830-1832 (2000).

Bakshi, R., et al; A double-blind, Placebo-controlled trial comparing the analgesic efficacy of two formulations of Diclofenac in postoperative dental pain; Current Therapeutic Research vol. 52, No. 3, pp. 435-442 Sep. 1992.

Dahlof, C., et al; Diclofenac-K (50 and 100 mg) and placebo in the acute treatment of migraine; Cephalalagia 13, pp. 20-26 (1993).

McNeely, w., et al; Diclofenac-Potasstum in Migraine: A Review; Drugs; 57; pp. 991-1003 (1999).

Mehlisch, D.R., et al; Single-dose therapy with Diclofenac potassium, aspirin, or placebo following dental impaction surgery, Today's Therapeutic Trends 12; (Suppl. 1) pp. 15-31 (1995).

The Didofenac-K/Sumatriptan Migrain Study Group; Acute treatment of migraine attacks: efficacy and safety of a nonsteroidal anti-inflammatory drug, diclofenac-potassium, in comparison to oral sumatriptan and placebo; Cephalalgia 19, pp. 232-240 (1999).

Ridgway, D.; Analgesics for Acute Pain, Meeting the United States and Food and Drug Administration's Requirements for Proof of Efficacy, Clin. J. Pain vol. 20, No. 3, May/Jun. pp. 123-132 (2004).

Diener, H-C, et al; Efficacy and tolerability of diclofenac potassium sachets in migraine: a randomized, double-blind, cross-over study in comparison with Diclofenac potassium tablets and placebo; Blackwell Publishing Ltd. Cephalalgia 26, pp. 537-547 (2005).

Hafele, C.M., et al; Efficacy and tolerability of diclofenac potassium sachets in acute postoperative dental pain: a placebo-controlled, randomised, comparative study vs diclofenac potassium tablets; 2006 Blackwell Publishing Ltd. Int. J Clin Pract, Mar. 2006, 60, 3, pp. 300-307.

Craig. CR.; Opioid and Nonopioid Analgesics, Modern Pharmacology 4th Edition, p. 437 (19+94).

Adkin, D.A., et al; The effect of different concentrations of Mannitol in solution on small intestinal transit; Implications for drug absorption; Pharmaceutical Research, vol. 12, No. 3 (1995).

Adkin, DA, et al; The effect of Mannitol on the oral bioavailability of Cimetidine; Journal of Pharmaceutical Sciences vol. 84, No. 12, Dec. 1995.

Kumar, A., et al.; The Mystery Ingredients: Sweeteners, Flavorings, Dyes and Preservatives in Analgesic/Antipyretic, Antihistamine/Decongestant, Cough and Cold, Antidiarrheal, and Liquid Theophylline Preparations; Pediatrics vol. 91 No. 5 May 1993.

Massiou. H., et al.; Effectiveness of oral diclofenac in the acute treatment of common migraine attacks: a double-blind study versus placebo; Cephalalgia 11 (1991).

Del Bene, E., et al; Intramuscular Treatment of Migraine Attacks Using Diclofenac Sodium; A Crossover Clinical Trial; The Journal of International Medical Research; 15: 44-48 (1987).

Database Internet [Online] Feb. 2005, Novartis Pharma: Voltaren Dispers XP002434112 retrieved from Internet accession No. http://www.fachinfo.de/pdf/00/59/005941.pdf.

\* cited by examiner

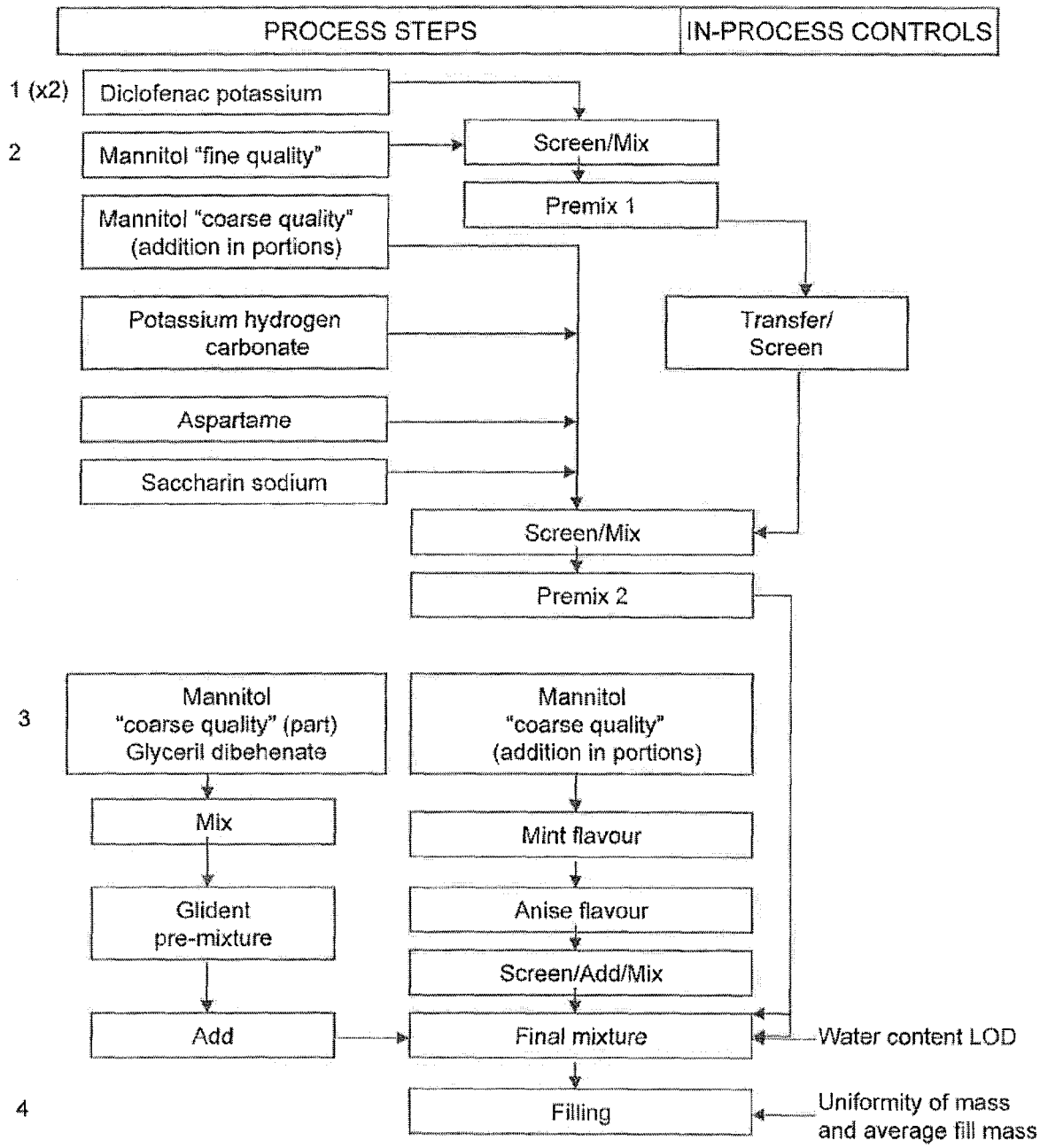

DICLOFENAC FORMULATIONS AND METHODS OF USE

RELATED APPLICATIONS

This application is a continuation of U.S. Ser. No. 12/399,175, filed Mar. 6, 2009, which is a continuation of U.S. Ser. No. 11/455,120, filed Jun. 16, 2006 and granted as U.S. Pat. No. 7,759,395, and claims priority under 35 U.S.C. §119(e) to U.S. Provisional Patent Application Nos. 60/692,024 (filed Jun. 17, 2005), and 60/691,757 (filed Jun. 17, 2005).

FIELD OF THE INVENTION

This invention concerns methods and formulations for treating migraine and other acute pain episodes using diclofenac, and formulations of diclofenac that provide both rapid and sustained relief from acute pain. The invention further concerns methods and formulations for treating symptoms that often accompany migraine and acute pain such as rebound headache, photophobia, phonophobia, nausea and vomiting.

BACKGROUND OF THE INVENTION

Diclofenac is a non-steroidal anti-inflammatory drug ("NSAID") known chemically as [(2,6-dichloro-anilino)-2-phenyl]-2-acetic acid. The drug was developed in the 1960s by scientists at Ciba-Geigy and is sold around the world by Novartis under various trade names, including Cataflam® and Voltaren® in the United States. A wet granulated formulation of diclofenac potassium was recently developed to provide an increased rate of absorption, and its pharmacokinetic properties tested against commercially available diclofenac potassium tablets. (Reiner et al., Increased absorption rate of diclofenac from fast acting formulations containing its potassium salt. Arzniem.-Forsch./Drug Res. 2001; 51:885-890.) According to the authors, the granular formulation showed a higher $C_{max}$ than the diclofenac potassium tablets, a shorter t. (i.e. time to $C_{max}$) and a similar AUC when compared to the tablet form.

Owing to its excellent analgesic properties, diclofenac is widely used for treating various types of pain, including both chronic and acute painful episodes. The drug is administered for the treatment of musculoskeletal and joint disorders such as rheumatoid arthritis, osteoarthritis, and ankylosing spondylitis; periarticular disorders such as bursitis and tendonitis; soft tissue disorders such as sprains and strains, and other painful conditions such as renal colic, acute gout, dysmenorrhoea, and following some surgical procedures. (Martindale (2000) Diclofenac. In: Reynolds, The Extra Pharmacopoeia. London: The Pharmaceutical Press; p. 31-33.) Diclofenac has also been studied for the treatment of headache pain from migraine attacks, using various doses and dosage forms, including 75 mg. intramuscular injections (Del Bene et al., Intramuscular treatment of migraine attacks using diclofenac sodium: a cross-over trial. J. Int. Med. Res. 1987; 1544-8), 100 mg. suppositories (Del Bene et al., Migraine attack treatment with diclofenac sodium. Cephalalgia 1985; 5:144-5), and 50 mg. enteric coated tablets. (Massiou et al., Effectiveness of oral diclofenac in the acute treatment of common migraine attacks: a double blind study versus placebo. Cephalalgia 1991; 1:59-63.)

Migraine attacks manifest a diverse array of symptoms that must be resolved in order for a treatment to be deemed truly effective against migraine (instead of just treating the symptoms). In particular, the treatment must be effective against the pain, photophobia, phonophobia and nausea that are caused by migraine, and it must be effective within the first two hours of treatment, in order to be considered a true treatment for migraine. None of the studies reported to date suggests that a 50 mg. diclofenac product could treat all of these symptoms within two hours of treatment.

In 1993, investigators studied 100 mg. and 50 mg. diclofenac tablets, in comparison to placebo, and determined that both strengths were effective against migraine pain within two hours of treatment, but that only the 100 mg. strength was effective against phonophobia and photophobia within two hours. (Dahlof et al., Diclofenac-K (50 and 100 mg.) and placebo in the acute treatment of migraine. Cephalalgia 1993; 13:117-123). In 1999, a separate group of investigators tested 50 mg. and 100 mg. sugar coated tablets of diclofenac potassium to treat migraine, and once again confirmed the ability of both doses to relieve migraine pain within two hours of treatment. (The Diclofenac-K/Sumatriptan Migraine Study Group, Acute treatment of migraine attacks: efficacy and safety of a nonsteroidal anti-inflammatory drug, diclofenac potassium, in comparison to oral sumatriptan and placebo. Cephalalgia 1999; 19:232-40.) The investigators concluded that neither dose was effective against photophobia two hours after treatment, that both doses were effective against photophobia eight hours after treatment, that only the 100 mg dose was effective against phonophobia two hours after treatment, and that the 50 mg dose was effective against photophobia eight hours after treatment.

The 1999 investigators also studied the effectiveness of 100 mg and 50 mg. diclofenac-K immediate release tablets at preventing recurrence of headaches within 48 hours of treatment. The investigators concluded that patients treated with the 50 mg and the 100 mg diclofenac-K tablets actually had a higher incidence of headache recurrence than patients treated with placebo (i.e. that the diclofenac-K performed worse than placebo), although the statistical significance of these findings is not reported.

This latter finding is consistent with other recent literature which recommends the use of a "long acting NSAID" to reduce the frequency of rebound headaches. For example, Plachetka recommends in U.S. Pat. No. 6,586,458 that triptan therapy be augmented with a "long acting NSAID" to provide "a substantial reduction in the frequency [of] relapse of headaches." Diclofenac potassium is not considered a long acting NSAID because it displays an average $C_{max}$ within only about one hour and a terminal half life of only about 1.9 hours when administered in commercially available sugar coated tablets.

Diclofenac is generally taken orally in the form of normal tablets or tablets covered with coatings resistant to gastric juices, or rectally, or by injection, or topically. Recently, however, in WO 97/44023, Reiner et al. proposed to administer diclofenac in a number of less conventional dosage forms—including as a powder sachet for oral administration after dissolving in water—for quicker onset of analgesic relief. One of the primary obstacles in the manufacture of powder sachets is the distribution of the drug in the powder, and the uniformity of content in the finished product. These hurdles are magnified in the production of diclofenac sachets due to the poor aftertaste of diclofenac, and the need to incorporate additional ingredients to compensate for this poor taste.

To ensure an adequately homogenous distribution of drug product in the bulk powder, Reiner et al. disclose a wet granulation process for manufacturing the powder sachets. In the first step of the process, a wet granulate is prepared from diclofenac potassium, potassium bicarbonate, saccharin, aspartame and mannitol, using 95% ethanol as the wetting agent. The granulate is then mixed with over one gram of sugar (saccharose) and various flavoring agents to improve the taste of the composition.

The method described by Reiner et al. produces an excellent pharmaceutical dosage form but suffers from a number of disadvantages including the size of the sachet (2 g) which makes the sachet more difficult to dissolve, and the presence of sugar in the formulation, which should be avoided in the diabetic population. In addition, the process requires precise controls on the granulometric process to assure uniform distribution of drug in the granulate and consistent amounts of drug in the finished product. What is needed is an alternative method for producing sugar-free powder diclofenac sachets and other fast acting dosage forms of diclofenac.

SUMMARY OF INVENTION

The inventors have unexpectedly discovered that rapidly bioavailable formulations of diclofenac are effective in the treatment of migraine and other acute pain episodes, and that in spite of their quick onset of action, they provide sustained relief against acute pain for up to twenty-four hours. Contrary to the prior art, which suggests that a long acting NSAID should be used to prevent rebound headache, and that a rapidly bioavailable formulation of diclofenac would be ineffective against rebound headache, the inventors have discovered that a rapidly bioavailable formulation of diclofenac, as measured by $t_{max}$ and $C_{max}$, prevents recurrence of headaches for at least twenty four hours after treatment in a significant population of migraine sufferers. In addition, the consistency of bioavailability seems to improve as the bioavailability of the molecules becomes more rapid, which further contributes to the clinical efficacy observed for these formulations.

The inventors have also surprisingly discovered that these rapidly bioavailable formulations relieve symptoms often associated with migraine and other acute pain, including photophobia and phonophobia, better than conventional immediate release tablets. These results are surprisingly seen even though the diclofenac in these formulations is more rapidly eliminated from the bloodstream than conventional immediate release tablets of diclofenac, and even though the total amount of diclofenac absorbed in the blood stream (measured as the area under the curve (i.e. $AUC_{0-\infty}$)) is comparable for the two formulations. The formulations are thus able to meet all of the primary clinical endpoints for evaluating migraine treatments, and for completely treating migraine.

Therefore, in one embodiment the invention preferably provides a method of treating migraine comprising: (a) providing a liquid formulation comprising 50 mg. of diclofenac or a pharmaceutically acceptable salt thereof, wherein said formulation: (i) is provided as a unit dose powder formulation and dissolved or suspended in water immediately before administration, or as a unit dose liquid formulation that is ingested with or without further mixing; (ii) achieves $t_{max}$ in from about 10 to about 20 minutes; and (iii) optionally but preferably achieves a $C_{max}$ of from about 1500 to about 2500 ng/ml; and (b) orally administering said formulation to a patient suffering from migraine, wherein migraine is defined as a disease manifested in a population of patients by periodic attacks of headache pain, nausea, photophobia and phonophobia. In one particular embodiment the method is used to treat migraine that is accompanied by photophobia and/or phonophobia. In another particular embodiment, the method is used to treat migraine patients who suffer from recurrent headache, and are diagnosed as requiring relief from recurrent headache within twenty-four hours of the initial treatment.

In other embodiments the method is used to treat any episode of acute pain in which the pain would otherwise persist for at least about eight hours, and pain relief is required for this time period. Thus, in still another embodiment the invention preferably provides a method of treating acute pain in a human patient requiring pain relief for at least eight hours, comprising: (a) providing an oral formulation comprising about 50 mg. of diclofenac or a pharmaceutically acceptable salt thereof, wherein said formulation (ii) achieves $t_{max}$ in from about 10 to about 35, 30, or 25 minutes; and (iii) optionally but preferably achieves a $C_{max}$ of from about 1400 or 1500 to about 2500 ng/ml; and (b) orally administering said formulation to a patient suffering from acute pain, preferably no more than 3 total times in a 24 hour period.

In still another embodiment the invention provides an alternative method for preparing powder diclofenac sachets that is based predominantly on the large proportion of mannitol in the formulation, which preferably includes a precise control of particle size of diluents in the finished product. The large proportion of mannitol imparts surprisingly rapid bioavailability to the formulation, while the control of particle size assures uniform distribution of diclofenac in the material used to fill the sachets and consistent amounts of drug in each sachet without the use of sugar or large amounts of diluent as taught in the prior art. The method and powders produced by the method are characterized by, among other variables, (1) the ratio of the diluent to the diclofenac in the powder, (2) a combination of particle sizes of the diluent in the final composition, and (3) the sequence of mixing the diclofenac and the varying particle sizes of diluent.

The invention further provides methods for manufacturing highly concentrated liquid formulations of diclofenac that can be drawn as drops from a bottle and administered after mixing the diclofenac with a suitable carrier such as water. In one aspect of this embodiment the invention provides a method of making a liquid solution of diclofenac, wherein the diclofenac is present in the liquid at a concentration of from about 10 to about 100 mg./ml., comprising (a) dissolving diclofenac in ethyl alcohol to form a solution, (b) mixing said solution with glycerol to form a second solution, and (c) mixing said second solution with water.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE DRAWING

The accompanying drawing, which is incorporated in and constitutes a part of this specification, illustrates several embodiments of the invention and together with the description, serves to explain the principles of the invention.

FIG. 1 is a flow diagram illustrating a non-granulate method and sequence of mixing employed in making 900 mg. powder sachets of the instant invention that contain 50 mg. of diclofenac potassium.

DETAILED DESCRIPTION OF THE INVENTION

The present invention may be understood more readily by reference to the following detailed description of preferred embodiments of the invention and the Examples included therein.

Methods of Treating Migraine and Acute Pain

As discussed above, the invention provides novel formulations of diclofenac—especially diclofenac potassium—that have proven to be remarkably effective against migraine headache and other forms of acute pain. The formulations may contain various quantities of diclofenac, in various oral dosage forms, ranging from about 12.5 mg. to about 100 mg. of diclofenac or a pharmaceutically acceptable salt thereof. Thus, for example, the formulation can contain about 12.5, 25, 37.5, 50, 75 or 100 mg of diclofenac or a pharmaceutically acceptable salt thereof, in a tablet, a capsule, a powder for oral solution, an oral solution or suspension, on orally dissolving tablet, a mucoadhesive film, or any other orally ingestable dosage form. In a particularly preferred embodiment, however, the formulations of the present invention are present in a liquid form when ingested, and they contain about 50 mg. of diclofenac or a pharmaceutically acceptable salt thereof. In another preferred embodiment, the formulations are used to treat migraine headache.

Therefore, in one embodiment the invention provides a method of treating migraine comprising: (a) providing a liquid formulation comprising 50 mg. of diclofenac or a pharmaceutically acceptable salt thereof, wherein said formulation: (i) is provided as a unit dose powder formulation and dissolved or suspended in water immediately before administration, or as a unit dose liquid formulation that is ingested with or without further mixing; (ii) achieves $t_{max}$ in from about 10 to about 20 minutes; (iii) optionally but preferably achieves a $C_{max}$ of from about 1500 to about 2500 ng/ml; and (b) orally administering said formulation to a patient suffering from migraine, wherein migraine is defined as a disease manifested in a population of patients by periodic attacks of headache pain, nausea, photophobia and phonophobia.

In one particular embodiment, the methods of this invention are used to treat some of the most difficult to treat migraine patients—i.e. those whose headache pain is likely to recur within twenty-four hours of initial treatment, or those who also suffer from photophobia or phonophobia. Therefore, in another embodiment the invention provides a method of treating migraine in a human patient suffering from migraine comprising: (a) providing a liquid formulation comprising about 50 mg. of diclofenac or a pharmaceutically acceptable salt thereof, wherein said formulation: (i) is provided as a powder formulation and dissolved or suspended in water immediately before administration, or as a liquid formulation that is ingested with or without further mixing; (ii) achieves $t_{max}$ in from about 10 to about 20 minutes; (iii) optionally but preferably achieves a $C_{max}$ of from about 1500 to about 2500 ng/ml; and (b) diagnosing a patient suffering from migraine as requiring sustained migraine relief for at least 24 hours (such as a patient who is susceptible to rebound or recurrent headaches); and (c) orally administering said formulation to said patient.

Patients who are particularly well-suited for treatment by the methods of this invention are those patients who have previously been treated for migraine pain using an acute pain medication, but who continued to suffer from symptoms such as phonophobia, photophobia, nausea and vomiting, especially those individuals who required additional medication for these symptoms. Thus, for example, in one embodiment the patient has previously been diagnosed as requiring relief from photophobia, phonophobia, nausea or vomiting in conjunction with treatment for migraine pain. In another embodiment the method is performed without administering other medications for the relief of photophobia, phonophobia, nausea or vomiting. In still another embodiment the method is performed without administering other medications for the relief of migraine pain.

Therefore, in still another embodiment the invention provides a method of treating migraine associated with phonophobia or photophobia in a human patient comprising: (a) providing a liquid formulation comprising 50 mg. of diclofenac or a pharmaceutically acceptable salt thereof, wherein said formulation: (i) is provided as a powder formulation and dissolved or suspended in water immediately before administration, or as a liquid formulation that is ingested with or without further mixing; (ii) achieves $t_{max}$ in from about 10 to about 20 minutes; (iii) optionally but preferably achieves a $C_{max}$ of from about 1500 to about 2500 ng/ml; and (b) orally administering said formulation to a patient suffering from migraine associated with photophobia or phonophobia.

As discussed above, this invention also concerns methods for treating acute pain using diclofenac, and formulations of diclofenac that provide immediate and sustained relief from any type of acute pain. In addition to migraine headache pain, the pain may derive from a variety of sources, including musculoskeletal and joint disorders such as rheumatoid arthritis, osteoarthritis, and ankylosing spondylitis, periarticular disorders such as bursitis and tendonitis, soft tissue disorders such as sprains and strains, and other painful conditions such as renal colic, acute gout, dysmenorrhoea, and following some surgical procedures. In one preferred embodiment the acute pain is post-operative pain, such as post-operative dental pain.

The formulations are particularly well suited for providing relief from sustained acute pain, defined herein as acute pain that would otherwise persist for about 4, 6 or 8 hours without the treatment contemplated by the current invention. In one preferred embodiment the patient treated by the method has been previously diagnosed as requiring relief from sustained acute pain. A patient requiring sustained relief from acute pain is a patient who has either been previously diagnosed as requiring rescue medication within about 4, 6 or 8 hours of treatment for said acute pain, or a patient whose acute pain is expected to persist for 4, 6 or 8 or more hours in the absence of treatment.

In another embodiment, therefore, the invention provides a method of treating acute pain in a human patient requiring pain relief for at least eight hours, comprising: (a) providing an oral formulation comprising about 50 mg. of diclofenac or a pharmaceutically acceptable salt thereof, wherein said formulation: (i) achieves a $C_{max}$ of from about 1400, 1450 or 1500 to about 2500 ng/ml; and (ii) achieves $t_{max}$ in from about 10 to about 35, 30 or 25 minutes; and (b) orally administering said formulation to a patient suffering from acute pain, preferably no more than 3 total times in a 24 hour period.

The sustained relief provided by the compositions of the present invention provides numerous advantages in the treatment of acute pain, and leads to decreased requirements for pain medication by many patients. Thus, in one embodiment the method is performed without administering other immediate pain relief or rescue medications within the first 4, 6 or 8 hours of administering the diclofenac formulation. In one embodiment, the formulation is administered no more than 3 total times in a 24 hour period. In another embodiment, the formulation is administered as needed for pain every 2, 4, 6 or 8 hours (or every 4-6, 4-8, or 6-8 hours), as needed for pain, preferably not to exceed three times per day. In yet another embodiment, the formulation is administered once every eight hours.

As discussed above, the formulations of the present invention are preferably administered as a liquid for oral ingestion, and can be provided in any form suitable for such administration. In a particularly preferred embodiment, the formulation is provided in a single unit dose as a powder sachet, which is mixed with water before administration. In other embodiments the formulation is already dissolved in a liquid, as in the drop formulation of the present invention and the unit dose vials discussed elsewhere herein. It will be understood, however, that the relief from migraine and acute pain occasioned by the methods of the present invention can be achieved with any oral formulation that achieves the pharmacokinetics described herein, and that the invention extends to any such dosage form.

Statistically Significant Relief

In some embodiments of the present invention, the medication is administered to a plurality of patients suffering from migraine, and statistically significant relief is observed based on one or more primary or secondary clinical endpoints, in comparison to placebo or 50 mg. immediate release diclofenac potassium tablets (i.e. Cataflam), including:

two hour pain relief (i.e. a decrease in pain intensity from moderate/severe to mild/none)
pain free at two hours
sustained pain relief for 6, 8 or 24 hours
relief from phonophobia at two hours
relief from photophobia at two hours
relief from nausea and vomiting at two hours As noted above, the ability to attain statistically significant relief by the methods of the present invention is greatly influenced by the coefficients of variation in Cmax and tmax observed for this invention, which seem to decrease as the diclofenac in these formulations becomes more bioavailable.

Of course, every patient treated by the methods of the present invention will not require relief from every clinical endpoint, or obtain relief from every clinical endpoint. In addition, the plurality of patients that any individual physician or physician's practice group treats may not rise to the level of "statistical significance," as that term is typically used in the pharmaceutical industry (i.e. p<0.05). In the context of this invention, the term "statistically significant" is not based solely upon the plurality of patients treated by the defined method, but takes into account well designed comparative clinical trials versus placebo that have previously been conducted to confirm the statistically significant relief, in addition to the clinical results obtained by practice of the present invention by individual patients, practitioners, or physician practice groups.

Pharmacokinetics

In one embodiment the composition is characterized by its pharmacokinetics, such as $C_{max}$ (i.e. average concentration of active chemical in the bloodstream after oral ingestion, preferably in the fasted state), and its $t_{max}$ (i.e. average time to reach said $C_{max}$, in a fasted state). In a particularly preferred embodiment, the mean $C_{max}$ for a 50 mg. diclofenac composition ranges from about 1300, 1400, 1500, 1600 or 1700 to about 2600, 2500, 2300, 2100, 2000 or 1900 ng/ml. A suitable range can be derived from any of these upper and lower bounds, but in one embodiment the formulation preferably attains a $C_{max}$ of from about 1300, 1400 or 1500 to about 2500 ng/ml; or from about 1500, 1600, or 1700 to about 2100 ng/ml, for a 50 mg. diclofenac formulation. It will be understood, of course that any of these $C_{max}$ values can be normalized based on the dose administered. Thus, for example, a 1500 ng/ml $C_{max}$ observed for a 50 mg. dose could be normalized to 30 ng/ml·g and applied to other dose amounts. In a particularly preferred embodiment the formulations yield only one peak concentration when blood concentrations are plotted against time.

The median $t_{max}$ (i.e. time to reach $C_{max}$) of the formulations is preferably from about 5 or 10 to about 40, 35, 30, 25 or 20 minutes. Once again, a suitable range can be derived from any of these upper and lower bounds, but in one particular embodiment the $t_{max}$ of the formulation is most preferably from about 10 to about 35 minutes, from about 10 to about 30 minutes, from about 10 to about 25 minutes, or from about 10 to about 20 minutes. The inter-subject coefficient of variability for said $C_{max}$ preferably is less than about 70, 65, 60, 55, 50, 40 or 35%, and the inter-subject coefficient of variability for said $t_{max}$ is preferably less than about 70, 60, 50, 40 or 35%.

Of course, it will be understood that bioavailability can differ from different study sites. When a single formulation gives results that vary significantly among different clinical sites and investigators, the results can be proportionately normalized against the bioavailability of Cataflam tablets, based upon the results reported in the examples hereto. Thus, for example, if the $C_{max}$ that a laboratory observes for Cataflam is only 750 ng/ml, all of the $C_{max}$ results reported from the laboratory could be adjusted by a factor of (1037.124)/(750).

Methods of Formulation

As noted previously, the invention also concerns methods of making a particulate flowable diclofenac composition that can be defined by a number of characteristics, including the presence of a fine powdered diluent, the combination of fine and coarse diluent, the total amount of diluent, the size distribution of diclofenac particles, or the use of a non-hygroscopic diluent. These various features and aspects of the present invention are set forth in greater detail below.

Diclofenac

The diclofenac used in the present invention can be defined by various parameters. In one embodiment, the raw material will be a powder that exhibits no more than 0.5 wt. % loss on drying. In another embodiment not less than 90% of the diclofenac particles are less than 500 micrometers in diameter, not less than 40% and not more than 70% of the particles are less than 200 micrometers in diameter, not less than 35% and not more than 65% of the particles are less than 150 micrometers in diameter, and not less than 30% of the particles are less than 100 micrometers in diameter. (Analyses performed using sieves according to the Sieve Test 2.9.12 Eur.Ph.—Alpine Air Jet Sieve.) The average particle size for the diclofenac powder is preferably about 150, 160, 170, 180, 190, 200, 210, 220, 230, or 240 micrometers, and can range between any two of the foregoing variables (i.e. from about 150 to about 230 micrometers, or from about 170 to about 220 micrometers).

The diclofenac can be present in acid or salt form although, owing to its poor solubility in water, diclofenac is normally used in salt form. The salts of diclofenac customarily used are those of sodium, potassium or other alkali and alkaline earth metals, together with salts of organic nature, such as the salts of basic amino acids, such as lysine, arginine and ornithine, or other pharmacologically acceptable organic bases which have the ability to render the resulting salt soluble in water. Diclofenac potassium is preferably used in this invention due to its fast onset of action.

In a preferred embodiment, 50 mg. of diclofenac or its salt is used in the final dosage form, although other amounts could be used including 12.5, 25, 37.5, 50, 75 or 100 mg of diclofenac, or a range having as endpoints any of the foregoing amounts. The amount of diclofenac preferably does not vary by more than about 95-105% from dose to dose.

Buffering Agents

Buffering agents are not critical to the invention, but are preferably used to provide a rapid rate of onset for the final pharmaceutical product. In a preferred embodiment for powder sachets, the buffering agent controls the pH of the formulation when dissolved in water, and preferably yields a pH greater than about 6.8, 7.0, 7.2, or 7.4, and less than about 7.8, 7.7 or 7.6, when mixed with 50 ml or 100 or 200 ml. of water at 25 degrees Celsius.

Particularly preferred buffering agents are alkali metal carbonates and bicarbonates and these agents are preferably employed in a weight ratio relative to the diclofenac of greater than about 1:5, 2:5, 2:1, 3:1 or 5:1. If desired, an upper limit on the buffer:diclofenac ratio can be placed at about 20:1, 10:1, 5:1, 1:1, 4:5 or 3:5. Ranges can be selected from any two of the foregoing values that are mathematically possible. In a preferred embodiment, the buffer:diclofenac weight ratio ranges from about 1:5 to about 4:5. Particularly preferred alkali metal bicarbonates are sodium bicarbonate and potassium bicarbonate.

Final Powdered Sachet Product

The powder sachets used in the methods of this invention can be produced by various methods including dry granulation, wet granulation and dry admixing processes. A suitable product produced by wet granulation is described, for example, by Reiner et al. in WO 97/44023.

In one clinical trial, a representative 50 mg. diclofenac formulation obtained by the method disclosed in examples 3 and 4 was shown to exhibit the following pharmacokinetic properties:

| | |
|---|---|
| $C_{max}$ mean value | 1620 ng/ml (CV = 53.8%) |
| $t_{max}$ mean value | 13.98 min (CV = 32.2%) |
| AUC 0-t mean value | 1010 (CV = 42.4%) |

In contrast, a 50 mg. formulation prepared by the wet granulation process disclosed in WO 97/44023 has been shown to exhibit the following pharmacokinetic properties:

| | |
|---|---|
| $C_{max}$ mean value | 2213 ng/ml (CV = 33.57%) |
| $t_{max}$ mean value | 13.68 min (CV = 16.3%) |
| AUC 0-t mean value | 1332.99 (CV = 26.86%) |

In one embodiment the powdered sachet is produced by a dry mixing process and is characterized by the presence of diclofenac particles having one of the particle size distributions described above. In another embodiment the product is characterized by the total amount of powder used to fill a sachet, which is preferably greater than 500, 600, 700 or 800 mg., and/or less than 1800, 1600, 1400, 1200, or 1000 mg., based on a 50 mg. diclofenac sachet. A preferred amount of powder is 900 mg. and the amount preferably does not vary outside the 855-945 mg/sachet range per package.

In still another embodiment the invention is characterized by the solubility of the product in water, the amount of water required to solubilize the product, and the time required to solubilize the product in a given amount of water. Therefore, in one embodiment a unit dose of the sachet is greater than 75% or 85% soluble or is completely soluble in 50 ml. of water at 25 degrees Celsius. In another embodiment the unit dose is greater than 75% or 85% solubilized or is completely solubilized in 50 ml. of water with stirring at 25 degrees Celsius in less than 5 minutes. This optimized solubility seems to restrict absorption to a shorter part of the gastrointestinal tract, most likely contributing to the faster absorption rate and to the lower variability in the absorption compared to immediate release diclofenac potassium tablets.

The water content of the final product is preferably less than about 1.5%. The final product is also preferably free of sugar (saccharose), preferably includes as sweeteners aspartame and/or saccharin, and preferably includes as flavoring agents anise and/or mint.

Practically any container that maintains hermetic conditions could be used for packaging the powder sachets, though preferably the container consists of a sachet that is hermetically sealed in four directions to maintain the product in hermetic conditions during storage. The sachet is preferably made from a three-layer coupled paper/aluminum/polyethylene foil in which the weight of the paper is from about 0.475 to about 0.525 g/100 cm$^2$, the weight of the aluminum is from about 0.203 to about 0.229 g/100 cm$^2$, and the weight of the polyethylene is from about 0.295 to about 0.365 g/100 cm$^2$.

Diluents for Powder Sachets

Diluents or "filler excipients" are prefereably added to increase the resulting dosage units' bulk, and to improve blending characteristics. Freely soluble diluents are particularly preferred because they improve the solubility of the final product. The diluent preferably has a solubility in water at 25 degrees Celsius of greater than about 10, 15 or 20 g/100 ml. of water. A particularly preferred diluent is mannitol, which is substantially non-hygroscopic, and which has a solubility in water of 22 g/100 ml. Other suitable diluents include lactose, glucose, sucrose, xylitol, and especially lactilol monohydrate due to its beneficial non-hygroscopic properties.

The size of the diluent, and the order of adding the diluent during the mixing process, have also proven important in the practice of the present invention. In a preferred dry mixing process, the diclofenac is mixed with a fine diluent powder before any further processing to distribute the diclofenac and to preserve its flowability. In a preferred wet granulation method, the diclofenac is granulated along with coarse diluent powder before any further processing.

The particles sizes for two exemplary fine diluent powders are reported below:

| Powder 1 (preferred) | Powder 2 |
|---|---|
| Size Distribution (measured by laser) | |
| >250 µm: not more than 5% | >500 µm: not more than 10% |
| >100 µm: not more than 25% | >315 µm: not more than 25% |
| >20 µm: not less than 55% | >40 µm: not less than 60% |
| Size Distribution (measured with sieves) | |
| >150 µm not more than 2% | >250 µm not more than 10% |
| Average Particle Size (measure by laser) | |
| 50 micrometers | 160 micrometers |

The fine diluent powder can also be characterized by its average particle diameter, which can range from less than about 200, 180, 160, 140, 120, 100, or 80 micrometers, to greater than about 1, 5, 10, 20, 30 or 40 micrometers, with ranges defined between any two of the foregoing values. Most preferably, the fine diluent powder has an average particle size of about 50±40, 30, 20 or 10 micrometers.

As a still further alternative, the fine diluent can be characterized by its particle size relative to the diclofenac powder. In such an embodiment, the fine diluent is characterized by an average particle size of less that 100%, 80%, 60% or 40% of the average particle size of the diclofenac powder, and greater that about 5%, 10% or 20% of the average particle size of the diclofenac powder, again with ranges defined between any two of the foregoing values.

In a 50 mg. diclofenac sachet, the weight ratio of fine diluent to diclofenac in the final powder composition is preferably greater than about 1:5, 1:2, 1:1 or 1.2:1, and/or less than about 10:1, 6:1, 4:1, 3:1 or 2:1, with ranges defined between any two of the foregoing values. A preferred range of weight ratios is from about 1:1 to about 2:1. In a particularly preferred embodiment for a 50 mg. diclofenac sachet, the sachet comprises from about 50 to about 100 mg. of the fine diluent particles, from about 60 to about 85 mg. of fine diluent particles, or from about 70 to about 75 mg. of fine diluent particles.

Once the initial mixture of diclofenac and fine diluent powder is prepared in the preferred dry mixing process, a coarser diluent is preferably used to mix in the remaining components, preferably using a step-addition process in which successive amounts of the coarser diluent are added between each newly added ingredient. A preferred sequence of mixing, for the dry blending and wet granulation processes, is set forth in the examples hereto. As with the fine diluent, the coarser diluent is also preferably non-hygroscopic. In a preferred embodiment, the coarser diluent is the same chemical entity as the fine diluent powder, which is preferably mannitol. In one embodiment the coarse diluent is characterized by an average particle size that is greater than the average particle size of the fine diluent, and preferably has an average particle size greater than about 120%, 150% or 200% of the average particle size of the fine diluent, and less than about 1000%, 800% or 600% of the average particle size of the fine diluent, with ranges defined between any two of the foregoing values.

In an alternative embodiment the coarse diluent is defined by its particle size relative to the particle size of the diclofenac powder. In this embodiment, the coarse diluent preferably has an average particle size from about 60, 80 or 100% to about 1000, 800, 600, 400 or 200% of the average particle size of the diclofenac powder, with ranges defined between any two of the foregoing variables.

In a still further alternative, the coarse diluent can be characterized as having an average particle diameter of greater than about 75, 85, or 100 micrometers, and less than about 300, 250, 200, or 150 micrometers. In a particularly preferred embodiment, the coarse diluent powder has the following size distribution:
>315 µm: not more than 10%
>75 µm: not less than 90%

The amount of the coarse diluent is not critical, though it is typically added in an amount to bring the total sachet weight up to about 900 mg. in a 50 mg. diclofenac formulation. The total dosage form preferably comprises from about 200 to about 1500 mg., from about 400 to about 1000 mg., from about 500 to about 800 mg., or from about 600 to about 750 mg. of coarse diluent in a 50 mg. diclofenac sachet. In various embodiments, the weight ratio of coarse diluent to diclofenac in a 50 mg. diclofenac sachet is greater than about 2:1, 4:1, 6:1, 8:1 or 10:1, and less than about 40:1, 30:1, 20:1 or 15:1. A preferred range of weight ratios of the coarse diluent powder to the diclofenac in a 50 mg. diclofenac sachet is from about 10:1 to about 20:1.

The invention can also be defined by the total amount of non-hygroscopic diluent (fine and coarse) relative to the amount of diclofenac and, in various embodiments for a 50 mg. diclofenac sachet, the weight ratio is greater about 1.5:1, 2:1, 4:1, 6:1, 8:1, 10:1, or 12:1, and less than about 80:1, 60:1, 40:1, 30:1, 25:1 or 20:1. In other embodiments, the total weight of the non-hygroscopic diluent is greater than about 40%, 50%, 60% or 70%, and less than about 95%, 90% or 85% of the weight of the total composition in the sachet.

Alternative Doses and Diluent/Diclofenac Ratios

As discussed above, the foregoing weight ratios and relative quantities of diclofenac to fine diluent, coarse diluent and total diluent are given for a 50 mg. dilofenac sachet, preferably in a 900 mg. formulation. It will be understood that the total volume of the sachet can be divided or increased by various factors, such as 1.5, 2 or 4 while maintaining the foregoing weight ratios, to lower or increase the total amount of the diclofenac in the formulation. Thus, for example, a 900 mg. sachet containing 50 mg. of diclofenac potassium, 648 mg. of coarse diluent and 73 mg. of fine diluent, could be divided in two to provide a 450 mg. sachet containing 25 mg. of diclofenac potassium, 324 mg. of coarse diluent, and 36.5 mg. of fine diluent, or it could be divided in four to provide a 225 mg. sachet containing 12.5 mg. of diclofenac, 162 mg. of coarse diluent and 18.25 mg. of fine diluent.

It is also possible to simply divide the 50 mg. of diclofenac in the sachets described above in half, and provide 25 mg. diclofenac sachets while keeping the amounts of fine and coarse diluent substantially constant by, for example, basically doubling the ratios of fine diluent and coarse diluent to diclofenac reported above. Thus, for example, one could prepare 25 mg. of diclofenac in a 900 mg. sachet using substantially the same amounts of fine and coarse diluent as reported above, simply by dividing the total diclofenac in the formulation by two. Once again, the total volume of such a sachet could be divided or increased by various factors, such as 1.5, 2 or 4 while maintaining the revised weight ratios, to lower or increase the total amount of the diclofenac in the formulation.

Lubricants for Powder Sachets

While the use of lubricants is not strictly necessary, in a preferred embodiment they are added to the powder to prevent the powder from sticking to the metering machine in the final stage of filling the sachets. Suitable lubricants include magnesium stearate, stearic acid, hydrogenated castor oil, talc, or mixtures thereof, but a preferred lubricant is glycerol dibehenate. The lubricant is preferably present in an amount of from about 0.01 to about 2 wt. %, and preferably about 0.2% w/w, based on the weight of the powder composition.

In the method of manufacturing the product, the lubricant is preferably mixed with the diclofenac/fine diluent mixture as a separately prepared premix that also comprises diluent, albeit in a coarser particle size.

Powder Sachet Processing

In a preferred embodiment the powder sachets used in the invention are made by a dry blending process in which the diclofenac powder and other ingredients are added sequentially to successive batches of diluent. In a particularly preferred embodiment, the diclofenac is first blended with the fine diluent followed by the successive addition of coarse particulate and further inactive ingredients.

Therefore, in one embodiment the diclofenac composition is a particulate flowable diclofenac composition made by a process comprising: (a) mixing powdered diclofenac with a fine powdered diluent to form a first mixture; and (b) mixing said first mixture with a coarse powdered diluent to form a second mixture. The second mixture is preferably obtained by adding the first mixture to a predefined volume of the coarse diluent, which has preferably been pre-loaded into a mixing machine. In a further embodiment the method of making the composition additionally comprises:

a) mixing said second mixture with an alkali metal bicarbonate to form a third dry mixture;

b) mixing said third mixture with coarse diluent to form a fourth mixture;
c) mixing coarse diluent with a lubricant to form a fifth mixture; and
d) mixing said fourth and fifth mixtures.

While the preferred method of manufacturing the compositions of the present invention is dry blending, other methods can also be employed that do not depend on mixing of dry powders including wet granulation. For wet granulation, the binder can be added dry to the powder blend, or as a solution in the solvent. The solvent is usually ethanol, water, or a mixture of both. The actual granulation is performed in either a high-shear, or low-shear type mixer. Low-shear granulation requires cheaper equipment and produces a more porous granule. High-shear granulation is faster and affords good control over particle size.

Fluid bed wet granulation is a variation of the process in which the granulation and drying is carried out in the same vessel (a fluid bed granulator). The powder mix is fluidized by dry air inside a chamber. The binder solution is sprayed onto the fluidized powder to form the agglomerates. Air fluidizing continues until the agglomerates are dry. The process requires expensive equipment, but is simpler and produces a very porous low-density granule, which can result in faster drug dissolution. Slow drug dissolution is sometimes a problem associated with wet granulation, as the active ingredient is locked into the granule, and initial tablet disintegration liberates the granules rather than the primary drug particles.

In dry granulation, particle size enlargement is achieved by aggregating the powder particles under high pressure (i.e., by compaction) then milling the compressed material to the desired size. Fines generated by milling are recycled back through the compactor. The compression step is typically carried out in a roller compactor in which the powder is compressed between two rollers.

Therefore, in another embodiment the invention provides a method of making a wet granulated powder formulation of diclofenac comprising: (a) wet granulating an admixture of diclofenac (or a pharmaceutically acceptable salt thereof), a first portion of coarse mannitol, and a suitable bicarbonate to form a wet granulate; and (b) admixing said wet granulate with a second portion of coarse mannitol and fine mannitol. In another embodiment the invention provides a method of making a wet granulated powder formulation of diclofenac comprising: (a) wet granulating an admixture of diclofenac (or a pharmaceutically acceptable salt thereof), a first portion of mannitol and optionally a bicarbonate to form a wet granulate; and (b) admixing said wet granulate with a second portion of mannitol, wherein the weight ratio of mannitol and diclofenac in said final formulation is greater than about 1.5:1.

Further subembodiments of the foregoing principal embodiments can be defined by one or more of the following additional parameters:
  the wet granulation is performed in ethanol;
  the method further comprises admixing said wet granulate with glyceryl dibehenate.
  the wet granulate comprises from about 8 to about 15 weight parts diclofenac (preferably 10 to 13 weight parts), from about 12 to about 20 weight parts coarse mannitol (preferably 15 to 18 weight parts); and from about 3 to about 7 weight parts bicarbonate (preferably 4 to 6 weight parts).
  wet granulate including from about 8 to about 15 weight parts diclofenac (preferably 10 to 13 weight parts) is admixed with: from about 100 to about 160 weight parts coarse mannitol (preferably 120 to 140 weight parts); from about 12 to about 20 weight parts fine mannitol (preferably 14 to 18 weight parts); and from about 0.2 to about 0.7 weight parts glyceryl dibehenate (preferably 0.4 to 0.5 weight parts), preferably in sequential order while stirring.
  the formulation comprises: fine mannitol and diclofenac or a pharmaceutically acceptable salt thereof at a weight ratio of from about 1:2 to about 5:1, coarse mannitol and diclofenac or a pharmaceutically acceptable salt thereof at a weight ratio of from about 2:1 to about 40:1, wherein: said fine diluent has an average particle size of from about 10 to about 180 micrometers, said coarse diluent has an average particle size of from about 85 to about 250 micrometers, and said coarse diluent has an average particle size greater than the average particle size of said fine diluent.
  said mannitol comprises fine mannitol and coarse mannitol at a weight ratio of from about 1:5 to about 1:20; said fine mannitol has the following particle size distribution: 250 μm: not more than 5%; 100 μm: not more than 25%; 20 μm: not less than 55%; and said coarse diluent has the following particle size distribution: 315 μm: not more than 10%; and >75 μm: not less than 90%.
  A weight ratio of mannitol to diclofenac of greater about 1.5:1, 2:1, 4:1, 6:1, 8:1, 10:1, or 12:1, and less than about 80:1, 60:1, 40:1, 30:1, 25:1 or 20:1.
  Total mannitol percentage greater than about 40%, 50%, 60% or 70%, and less than about 95%, 90% or 85%, of the weight of the total composition in the sachet.

Liquid Formulations

The invention further provides methods for using diclofenac compositions that are provided as liquids having the diclofenac already dissolved therein. Practically any sort of single use "vial" can be used for containing a liquid dosage form. For purposes of this application, "vial" means a small glass container sealed with a suitable stopper and seal, or any other suitable container such as breakable and non-breakable glass and plastic vials, miniature screw-top jars, and any other type of container of a size capable of holding a small amount of diclofenac liquid. Thus, for example, when the diclofenac is formulated in liquid solutions that contain approximately 50 mg. diclofenac potassium in every ml. of liquid, the formulation can be packaged in a dropper bottle that contains any suitable quantity of liquid, typically from about 15 to about 100 ml. of solution. The concentration of diclofenac in these formulations typically will be about 50 mg/ml, but could range from about 10 to about 100 mg/ml, including 10, 25, 50, 75 and 100 mg./ml. Alternatively, the vial can be a single use vial, which would contain a suitable quantity of liquid such as about 15 ml. for a 50 mg. dose of diclofenac potassium.

As with the other formulations of this invention, buffering agents can be used in the drop formulations where a rapid rate of onset is desired for the final pharmaceutical product. In a preferred embodiment for the drop formulation, the buffering agent most preferably imparts a pH ranging from about 7 to about 1.5, from about 8 to about 10, from about 8.5 to about 9.5, and most preferably about 9.

Drop formulations are preferably prepared in a three step process comprising (a) dissolving diclofenac in ethyl alcohol to form a solution, (b) mixing said solution with glycerol to form a second solution, and (c) mixing said second solution with water to form a third solution. In a further embodiment, a fourth solution is made by dissolving any desired buffers in water, which is then mixed with the third solution to provide a final solution. The final solution preferably comprises from about 35 to about 45 wt. % water, from about 25 to about 35 wt. % ethyl alcohol, and from about 15 to about 25 wt. % glycerol.

In another embodiment the liquid solution is characterized by its pharmacokinetics, such as $C_{max}$ (i.e. average concentration of active chemical in the bloodstream after oral ingestion), and its $t_{max}$ (i.e. average time to reach said $C_{max}$). A representative 50 mg. drop diclofenac formulation obtained by the method disclosed in examples 6 and 7 herein exhibits the following pharmacokinetic properties:

| | |
|---|---|
| $C_{max}$ mean value | 1679 ng/ml (CV = 39.85%) |
| $T_{max}$ mean value | 15.0 min (CV = 56%) |
| $AUC_{0-t}$ mean value | 1383 (CV = 30.59%) |

Capsule and Tablet Formulations

Examplary solid oral formulations contemplated by the present invention are set forth in Example 12. Preferred $C_{max}$ and $t_{max}$ ranges for tablet and capsule dosage forms of the invention are set forth below:

| | Mean $C_{max}$ (ng/ml) | Mean $t_{max}$ (min) |
|---|---|---|
| 50 mg. diclofenac tablet or capsule | 1300-2300; 1400-2200; 1500-2100; 1750-2000; 1600-1900 | 5-35; 10-30; 12-25; 15-20 |
| 25 mg. diclofenac tablet or capsule | 700-1150; 750-950; 800-900; 850-1050; 900-1000 | 5-35; 10-30; 15-30; 15-25 |
| 12.5 mg. diclofenac tablet or capsule | 350-650; 400-600; 450-550 | 5-35; 10-30; 15-25 |

Disintegration times for the tablet and capsule dosage forms of the present invention, when tested according to USP 28 <701>, are preferably less than about 20 minutes, 15 minutes, 10 minutes, 5 minutes, or even 4 minutes, and greater than about 1, 2 or 3 minutes, most preferably from about 3 to about 5 minutes. In one particular embodiment, the dosage form is a tablet, and the tablet has a disintegration time that increases as the hardness of the tablet decreases. In another embodiment, the tablet has a disintegration time that increases as the moisture absorption by the tablet increases.

Dissolution times for the tablet and capsule dosage forms of the present invention, when tested according to USP 28 <711>, based on the time it takes to dissolve 90 or 95 wt. % of the drug substance, are preferably less than about 20 minutes, 15 minutes, 10 minutes, 5 minutes, or even 3 minutes, and greater than about 1 or 2 minutes. In a preferred embodiment the dissolution profile of the dosage forms of the present invention is as follows: not less than 85, 90 or 95% after 15 minutes in simulated intestinal fluid (i.e. water) at pH=6.8.

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

Example 1

Comparative Study of Diclofenac-K Sachet, Diclofenac-K Tablets, and Placebo in Treatment of Migraine A randomized, double-blind, double-dummy multi-center, single dose, placebo- and active-controlled crossover study, with an eight hour evaluation was undertaken in adult migraine patients. 328 patients were randomized among treatments and a comparison made among treatments with a 50 mg. diclofenac potassium sachet formulation, the 50 mg. diclofenac potassium sugar coated tablet marketed commercially as Cataflam®, and placebo. Results are reported in Table 1.

TABLE 1

| | Pain on Verbal Scale | | |
|---|---|---|---|
| Parameter | Diclofenac-K Sachet % of patients | Diclofenac-K Tablet % of patients | Placebo % of patients |
| Pain free at 2 hours | | | |
| ITT pop | 24.7% | 18.5% | 11.7% |
| PP pop | 23.6% | 17.8% | 12.9% |
| Mod-sev baseline pain | 24.2% | 17.0% | 12.5% |
| Headache response 2 hours | 46.0% | 41.6% | 24.1% |
| Sustained response | 36.8% | 30.9% | 18.4% |
| Sustained pain free | 22.3% | 15.1% | 9.4% |

Example 2

Comparative Study of Diclofenac-K Sachet, Diclofenac-K Tablets, and Placebo in Treatment of Acute Dental Pain A double-blind, randomized, parallel-group trial compared the analgesic efficacy of single 50 mg doses of diclofenac potassium sachets and tablets with placebo in 184 patients with moderate/severe pain after extraction of impacted third molar(s). The primary efficacy variable was the average pain reduction from baseline during the first 2 hours after intake of study medication, assessed using a visual analog scale (VAS). During the first 2 hours post-dose sachets and tablets demonstrated significantly less pain (P<0.05) versus placebo and sachets were more effective than tablets (P<0.05). Onset of analgesic effect (VAS) was maintained for 8 hours for sachets and tablets (P<0.05). Fewer patients remedicated versus placebo and the results for pain relief and intensity assessed on a verbal scale confirmed the findings for VAS pain intensity. No safety issues were identified. Results are reported in Table 2.

TABLE 2

| Average VAS Pain Reduction from Baseline during the First 2 Hours (ITT Population) | | | | |
|---|---|---|---|---|
| Treatment effect and contrast | N | Average VAS pain reduction in mm | | |
| | | LS mean (SE) | 95% CI | P value[a] |
| Diclofenac Sachet | 73 | 36.3 (2.4) | 31.7-41.0 | <.0001 |
| Diclofenac Tablet | 71 | 29.1 (2.4) | 24.4-33.9 | <.0001 |

TABLE 2-continued

Average VAS Pain Reduction from Baseline
during the First 2 Hours (ITT Population)

| Treatment effect and contrast | N | Average VAS pain reduction in mm | | |
|---|---|---|---|---|
| | | LS mean (SE) | 95% CI | P value[a] |
| Placebo | 39 | 11.7 (3.1) | 5.5-17.8 | .0002 |
| Diclofenac Sachet - Placebo | — | 24.7 (3.8) | 17.3-32.1 | <.0001 (1) |
| Diclofenac Sachet - Diclofenac Tablet | — | 7.2 (3.1) | 1.0-13.4 | <.0001 (2) |
| Diclofenac Tablet - Placebo | — | 17.5 (3.8) | 10.0-24.9 | <.0001 (1) |

LS = least squares, SE—standard error of the mean, CI—confidence interval. All statistics for treatment effects and treatment contrasts are based on the analysis of covariance model: Average pain reduction = treatment + country + baseline VAS pain intensity.
[a]P values are two-sided for treatment effects (difference to 0), (1) one-sided P value for verum # placebo, (2) one-sided P value for diclofenac potassium sachet < diclofenac potassium tablet − 10 (non-inferiority test)

Example 3

Representative 900 mg. Powder Sachet Formulation

Table 3 describes the composition of a representative 900 mg. powder sachet formulation containing 50 g. of diclofenac potassium that is suitable for practicing the present invention.

TABLE 3

| Name of the component | Unit (mg.) | Function | Reference standard |
|---|---|---|---|
| Diclofenac potassium[1] | 50.0 | Active substance | Ph. Eur. |
| Glycerol dibehenate | 2.0 | Lubricant | Ph. Eur. |
| Saccharin sodium | 5.0 | Sweetening agent, Flavoring enhancer | Ph. Eur. |
| Anise flavor | 15.0 | Flavoring agent | In-house specifications |
| Potassium hydrogen Carbonate | 22.0 | Buffering agent | Ph. Eur. |
| Mint flavor | 35.0 | Flavoring agent | In-house specifications |
| Aspartame | 50.0 | Sweetening agent, Flavoring enhancer | Ph. Eur. |
| Mannitol[2] | 721.0 | Diluent | Ph. Eur. + additional specification |
| Total weight | 900.0 | | |

[1]Particle size distribution:
Not less than 90% ≤ 500 μm
Not less than 40% and not more than 70% ≤ 200 μm
Not less than 35% and not more than 65% ≤ 150 μm
Not less than 30% ≤ 100 μm
[2]As Mannitol "coarse quality" (648.0 mg) and Mannitol "fine quality" (73.0 mg).

Example 4

Manufacturing Process for 900 Mg. Powder Sachets Containing 50 mg. of Diclofenac Potassium A representative process for manufacturing 900 mg. powder sachets containing 50 mg. of diclofenac potassium is set forth below, using the equipment set forth in Table 1. The manufacture is performed under controlled temperature and relative humidity according to the following process.

| Step | |
|---|---|
| 1 | Sieve using a vibrating sieving machine (typically 850 μm) 47.45 Kg of Mannitol "fine quality" and 33.15 kg of Diclofenac Potassium. Load in a high shear mixer and mix for approx. 6 minutes. Repeat this step once. (pre-mixture 1) |
| 2 | Sieve using a vibrating sieving machine (typically 850 μm), and load in a convection mixer (in the following order) 120.0 kg of mannitol "coarse quality," the pre-mixture 1, 100.0 kg of mannitol "coarse quality," 28.6 kg of potassium hydrogen carbonate, 100.0 kg of mannitol "coarse quality," 65.0 kg of aspartame, 100.0 kg of mannitol "coarse quality," 6.5 kg of saccharin sodium and 100.0 kg of mannitol "coarse quality." Mix for approx. 5 minutes (pre-mixture 2). |
| 3 (final mixture) | Sieve using an oscillating sieving machine (typically 850 μm), and load in the convection mixer, in the following order, 72.4 kg of mannitol "coarse quality," 52.6 kg of the glidant pre-mixture consisting of 2.6 kg of Glyceryl dibehenate and 50.0 kg of mannitol "coarse quality," 45.5 kg of mint flavour, 100.0 kg of mannitol "coarse quality," 19.5 kg of anise flavour and 100.0 kg of mannitol "coarse quality." Mix for approx. 7 minutes in order to obtain the final homogenous mixture to fill into sachets. |
| 4 (filling) | Fill the final mixture into sachets at the target weight. |

TABLE 4

| Manufacturing equipment | |
| --- | --- |
| Unit operation | Type of equipment |
| Sieving | Screening mill, oscillating bar |
| Premixing (pre-mixture 1) | High shear mixer |
| Mixing (pre-mixture 2 and final mixture) | Convection mixer, planetary blenders |
| Filling into sachet | Powder filler, Volumetric filling station |

Example 5

Wet Granulated Powder Sachet Manufacturing Process

The manufacture of 50 mg. diclofenac potassium sachets having the formulation prescribed in Example 3, via wet granulation, is set forth in Tables 5 and 6.

TABLE 5

| Batch formula | |
| --- | --- |
| Name of the components | Amount (kg) |
| Diclofenac potassium | 11.25[1] |
| Glycerol dibehenate | 0.450 |
| Saccharin sodium | 1.125 |
| Anise flavour | 3.375 |
| Potassium hydrogen carbonate | 4.95 |
| Mint flavour | 7.875 |
| Aspartame | 11.25 |
| Mannitol "fine quality" | 16.425 |
| Mannitol "coarse quality" | 145.845 |
| Ethyl Alcohol | 3.88 * |
| Total | 202.5 |

* Eliminated during the drying process of the wet granulate.

TABLE 6

| Manufacturing process | |
| --- | --- |
| Step | |
| 1 | Load in a wet granulator 16.2 kg of mannitol "coarse quality," 11.25 kg of diclofenac potassium, 4.95 kg of potassium bicarbonate, 1.125 kg of saccharin sodium and 11.125 kg of aspartame; mix for approx. 5 minutes; add 3.88 kg of ethyl alcohol and mix for 5 minutes; load the wet granulate in oven at 50° C. until the humidity of granulate is below 1%. |
| 2 | Sieve using an oscillating sieving machine (typically 850 μm) the following excipients: mannitol "coarse quality," mannitol "fine quality," glyceryl dibehenate, mint flavour and anice flavour; load the granulate obtained in step 1 in a convection mixer and add, in the following order, 129.475 kg of mannitol "coarse quality," 16.425 kg of mannitol "fine quality," 0.45 kg of glyceryl dibehenate, 7.875 kg of mint flavour and 3.375 kg of anise flavour; mix for approx. 30 minutes |
| 3 | Fill the final mixture into sachets at the target weight. |

Example 6

Representative Drop Formulation (50 Mg. Diclofenac Potassium/ml. Of Solution)

Table 7 describes a representative formulation for a drop formulation of diclofenac in which one milliliter solution contains 50 mg. of diclofenac potassium. The formulation is administered by adding the drops to water and orally ingesting the mixture.

TABLE 7

| Drop Solution Composition | | | |
| --- | --- | --- | --- |
| Names of ingredients | Unit (g) | Function | Reference standards |
| Active ingredients | | | |
| Diclofenac potassium | 5.0[a] | Anti-inflammatory agent | Eur. Ph. |
| Solution excipients | | | |
| Ethyl alcohol | 30.0 | Solubilizing and preservative agent | Eur. Ph. |
| Glycerol | 20.0 | Solubilizing agent | Eur. Ph. |
| Potassium hydrogen carbonate | 2.5 | Buffering agent | Eur. Ph. |
| Saccharin sodium | 1.5 | Sweetening agent | Eur. Ph. |
| Caramel E 150a | 0.25 | Colouring agent | Int. standard[b] |
| Purified water | 42.9 | Diluent agent | Eur. Ph. |
| Total weight[b] | 102.15 | | |

[a]This amount refers to active substance material with 100.0% assay.
[b]Weight of 100.0 ml of solution (relative density = 1.0215 g/ml).

The formulation is preferably contained in a brown colored glass container, equipped with dropper and screw-cap closure, holding 20 or 100 ml of Diclofenac potassium solution. The glass container (type III) is suitable for liquid preparations that are for parenteral use. The dropper is made from polyethylene low density (PE-LD) material, according to food and pharmaceutical regulations. The screw cap is made from polypropylene, suitable as child proof closure.

Example 7

Manufacturing Process for Drop Formulation

The raw materials necessary for the production of a pilot standard batch of 250 liters of solution (volume required to fill 12,500 or 2,500 bottles with a capacity of 20 ml or 100 ml, respectively) are listed in Table 8.

TABLE 8

Manufacturing formula for a pilot standard
batch of 250 liters of solution

| Names of Ingredients | Unit (kg) |
|---|---|
| Active ingredients | |
| Diclofenac potassium[a] | 12.500 |
| Solution excipients | |
| Ethyl alcohol 96% | 75.000 |
| Glycerol | 50.000 |
| Potassium hydrogen carbonate | 6.250 |
| Saccharin sodium | 3.750 |
| Caramel E 150a | 0.625 |
| Purified water | 107.250 |
| Total weight[b] | 255.375 |

[a]Analytical specifications of Diclofenac potassium are the same used for the sachets
[b]Weight of 250 liters of solution (relative density 1.0215 g/ml).

12.5 kg of Diclofenac potassium, 6.25 kg of potassium hydrogen carbonate, 75 kg of ethyl alcohol 96%, 50 kg of glycerol, 3.75 kg of saccharin sodium, 0.625 kg of Caramel E 150a and two different amounts (76 kg and 31.25 kg) of purified water are first weighed.

A first mixture is then prepared by adding the ethyl alcohol 96% into a mixing vessel and then, under stirring, adding the active ingredient diclofenac potassium. After stirring for 10-15 minutes, the glycerol is added and the mixture stirred for another 10-15 minutes. While stirring, 76 kg of purified water is added to the mixture and stirred until a complete clear solution is obtained.

A second mixture is prepared by adding 31.25 kg of purified water into a separate mixing vessel and, under stirring, adding the remaining excipients (potassium hydrogen carbonate, saccharin sodium and Caramel E 150a). The mixture is stirred for 15-30 minutes.

While stirring, the first mixture is added to the second mixture and the resultant mixture stirred until a complete clear brown solution is obtained. Under mixing, water is added to the solution until a weight of 255.375 kg (250 liter of solution) is obtained. The solution is particle-free filtrated.

Example 8

Additional Drop Formulations (25 mg. Diclofenac Potassium/ml)

Tables 9 and 10 describe representative formulations of drops containing 25 mg. of diclofenac potassium per ml. of solution.

TABLE 9

| Names of ingredients | Unit(g) | Function | Reference standard |
|---|---|---|---|
| Active ingredients | | | |
| Diclofenac potassium | 2.50 | Anti-inflammatory agent | Eur. Ph. |
| Solution excipients | | | |
| Ethyl alcohol 96% | 30.00 | Solubilizing and preservative agent | Eur. Ph. |
| Glycerol | 20.00 | Solubilizing agent | Eur. Ph. |
| Potassium hydrogen carbonate | 1.25 | Buffering agent | Eur. Ph. |
| Saccharin sodium | 1.50 | Sweetening agent | Eur. Ph. |
| Acesulfame | 3.00 | Sweetening agent | Eur. Ph. |
| Caramel E 150a | 0.25 | Colouring agent | Int. standard |

TABLE 9-continued

| Names of ingredients | Unit(g) | Function | Reference standard |
|---|---|---|---|
| Mint flavour | 1.40 | Flavouring agent | Int. standard |
| Anise flavour | 0.60 | Flavouring agent | Int. standard |
| Purified water | Qb to 100 ml | Diluent agent | Eur. Ph. |
| Total volume | 100.00 | | |

TABLE 10

| Names of ingredients | Unit (g) | Function | Reference standard |
|---|---|---|---|
| Active ingredients | | | |
| Diclofenac potassium | 2.50 | Anti-inflammatory agent | Eur. Ph. |
| Solution excipients | | | |
| Ethyl alcohol 96% | 30.00 | Solubilizing and preservative agent | Eur. Ph. |
| Glycerol | 20.00 | Solubilizing agent | Eur. Ph. |
| Potassium hydrogen carbonate | 1.25 | Buffering agent | Eur. Ph. |
| Saccharin sodium | 1.50 | Sweetening agent | Eur. Ph. |
| Acesulfame | 3.00 | Sweetening agent | Eur. Ph. |
| Caramel E 150a | 0.25 | Colouring agent | Int. standard |
| Cola flavour | 2.00 | Flavouring agent | Int. standard |
| Purified water | qb a 100 ml | Diluent agent | Eur. Ph. |
| Total volume | 100.00 | | |

Example 9

900 mg. Powder Sachet Formulation Containing 25 mg of Diclofenac Sodium

The ingredients of the product diclofenac sodium 25 mg powder for oral solution (sachets, weighing 900.0 mg) are listed in Table 11 below.

TABLE 11

| Names of ingredients | Unit (mg.) | Function | Reference standard |
|---|---|---|---|
| Active ingredients | | | |
| Diclofenac sodium | 25[a] mg | Anti-inflammatory agent | Eur. Ph. |
| Excipients | | | |
| Potassium hydrogen carbonate | 11.0 mg | Buffering agent | Eur. Ph. |
| Mannitol[b] | 698.0 mg | Diluent agent | Eur. Ph. |
| Mannitol[c] | 74.00 g | Diluent agent | Eur. Ph. |
| Acesulfame Potassium | 40.0 mg | Sweetening agent | Eur. Ph. |
| Glycerol Dibehenate (compritol 888 ATO) | 2.0 mg | Lubricant agent | Eur. Ph. |
| Mint flavour | 15.0 mg | Flavouring agent | Manufacturer |
| Anise flavour | 35.0 mg | Flavouring agent | Manufacturer |
| Total weight | 900.0 mg | | |

[a]This amount refers to active substance material with 100.0% assay. The diclofenac sodium has the following particle size distribution: not less than 95% of the particles are less than 500 micrometers in diameter, not more than 90% are less than 250 micrometers in diameter, not more than 60% are less than 180 micrometers in diameter, and not more than 30% are less than 125 micrometers.
[b]Pearlitol SD 200, conform to Eur. Ph.
[c]Mannitol 35, conform to Eur. Ph..

Example 10

Method of Preparing 900 mg. Powder Sachets Containing 25 mg. Of Diclofenac Sodium A representative process for manufacturing 900 mg. powder sachets containing 25 mg. of diclofenac sodium is set forth below, using the equipment set forth in Table 1. The manufacture is performed under controlled temperature and relative humidity according to the following process.

Preparation of the Pre-Mixture

Sieve all the ingredients necessary for the production of the powder, then weigh 1.375 kg of diclofenac sodium, 0.605 kg of potassium hydrogen carbonate, 38.390 kg of mannitol (pearlitol SD 200), 4.070 kg of mannitol 35, 2.200 kg of acesulfame K, 0.825 kg of mint flavour, 1.930 kg of anise flavour and 0.11 kg of glyceryl dibehenate. Load in the mixer: diclofenac sodium, potassium hydrogen carbonate, mannitol 35, acesulfame K, mint flavour and anise flavour. Mix for 25 minutes.

Preparation of the Mixture

Transfer the premix into mixer; add mannitol SD 200 and glyceryl dibehenate, mix for 30 minutes.

Example 11

Diclofenac K Sachet Bioavailability Comparison

Test Formulations: Diclofenac potassium 50 mg powder for oral solution (Example 4)

Reference Formulation: Diclofenac potassium, 50 mg film-coated tablets, Cataflam by Novartis Pharma

TABLE 12

| | Test Formulation fasting | | | | | |
|---|---|---|---|---|---|---|
| Statistic | AUC(0-inf) (ng*hr/mL) | AUC(0-t) (ng*hr/mL) | Cmax (ng/mL) | Tmax (hr) | Kel (1/hr) | T½ (hr) |
| N | 32 | 33 | 33 | 33 | 32 | 32 |
| Geometric mean | 1201.001 | 1185.573 | 1505.296 | 0.264 | 0.54616 | 1.269 |
| Mean | 1232.925 | 1216.609 | 1586.502 | 0.277 | 0.56938 | 1.322 |
| SD | 283.9458 | 277.7587 | 513.3048 | 0.1035 | 0.167653 | 0.3803 |
| CV % | 23.03 | 22.83 | 32.35 | 37.32 | 29.45 | 28.76 |
| Median | 1177.67 | 1164.38 | 1528.20 | 0.25 | 0.5389 | 1.29 |
| Minimum | 686.48 | 668.10 | 800.58 | 0.17 | 0.3442 | 0.74 |
| Maximum | 1912.34 | 1896.02 | 2800.55 | 0.67 | 0.9352 | 2.01 |

TABLE 13

| | Cataflam fasting | | | | | |
|---|---|---|---|---|---|---|
| Statistic | AUC(0-inf) (ng*hr/mL) | AUC(0-t) (ng*hr/mL) | Cmax (ng/mL) | Tmax (hr) | Kel (1/hr) | T½ (hr) |
| N | 32 | 33 | 33 | 33 | 32 | 32 |
| Geometric mean | 1064.370 | 1045.187 | 1037.124 | 0.618 | 0.56098 | 1.236 |
| Mean | 1097.185 | 1077.596 | 1146.649 | 0.788 | 0.58669 | 1.290 |
| SD | 275.9971 | 272.7532 | 450.9879 | 0.7524 | 0.182630 | 0.3808 |
| CV % | 25.16 | 25.31 | 39.33 | 95.53 | 31.13 | 29.51 |
| Median | 1078.28 | 1059.80 | 1125.91 | 0.50 | 0.5843 | 1.19 |
| Minimum | 537.38 | 524.43 | 197.17 | 0.25 | 0.3378 | 0.63 |
| Maximum | 1975.32 | 1959.12 | 1972.74 | 4.00 | 1.1013 | 2.05 |

Example 12

50 mg. Diclofenac K Tablet Comparison

Test Formulations: T1: Diclofenac potassium 50 mg film-coated tablets, alcohol granulation T2: Diclofenac potassium 50 mg film-coated tablets, dry granulation Reference Formulation: Diclofenac potassium, 50 mg film-coated tablets, Voltarene® Rapid by Novartis Pharma Study design: Single dose, 3-way, crossover randomised on 6 healthy volunteers Blood samples drawn: 0 (pre-dose), 5, 10, 15, 20, 30, 45, 60, 90 min, 2, 3, 4, 5, 6, 8, 10, 12 h Assay: LC-MS-MS//LOQ 5 ng/ml

TABLE 14

Formulation of Comparison Tablets

| | T1, K salt, 50 mg, tablets | T2, K salt, 50 mg, tablets | Reference, K salt, 50 mg, Voltaren ® Rapid tablets |
|---|---|---|---|
| Description | Diclofenac potassium 50 mg film-coated tablets (by alcoholic granulation) | Diclofenac potassium 50 mg film-coated tablets (by direct compression) | Diclofenac potassium 50 mg film-coated tablets |
| Active ingredient | Diclofenac potassium mg 50 | Diclofenac potassium mg 50 | Diclofenac potassium mg 50 |
| Excipients | Potassium bicarbonate mg 22<br>Mannitol mg 50<br>Maize starch mg 25<br>Hydroxypropylmethylcellulose mg 0.2<br>Sodium laurylsulfate mg 0.1<br>Polyvinylpyrrolidone mg 1<br>Sodium starch glycollate mg 2.5<br>Magnesium stearate mg 4.5<br>Silicium aerosil FK 160 mg 1<br>Coating Opadry Clear (HPMC 2910 and polyethyleneglycol 400) mg 4 | Potassium bicarbonate mg 22<br>Mannitol 400 mg 119.9<br>Sodium laurylsulfate mg 0.1<br>Polyvinylpyrrolidone mg 6<br>Magnesium stearate mg 2<br>Film Coating Opadry Clear (HPMC 2910, polyethyleneglycol 400) mg 4 | Calcium phosphate<br>Saccharose<br>Maize starch<br>Talc<br>Sodium Carboxymethylcellulose<br>Colloidal anhydrous silicium<br>Polyvinylpyrrolidone<br>Microcrystalline cellulose<br>Magnesium stearate<br>Polyethylenglycole<br>Titanidioxide (E171)<br>Iron oxide red (E172) |
| Total weight | 160.3 mg | 204 mg | |

TABLE 15

Pharmacokinetics of Comparison Tablets

| | | PK results | | |
|---|---|---|---|---|
| | | Test 1 (K, tablets 50 mg) | Test 2 (K, tablets 50 mg) | Reference (K, tablets 50 mg) |
| $C_{max}$ | Mean | 1873.30 | 1744.8 | 1307.0 |
| | SD | 553.80 | 572.3 | 558.4 |
| | CV % | 29.5 | 32.8 | 42.7 |
| | Min | 1228.9 | 1057.4 | 581.8 |
| | Max | 2516.5 | 2468.9 | 1935.5 |
| AUC | Mean | 1219 | 1237 | 1168 |
| | SD | 246 | 276 | 282 |
| | CV % | 20.2 | 22.3 | 24.1 |
| | Min | 874 | 848 | 913 |
| | Max | 1615 | 1668 | 1642 |
| $t_{max}$ | Mean | 0.31 h (18.6 min) | 0.28 h (16.8 min) | 0.68 h (40.8 min) |
| | SD | 0.04 | 0.07 | 0.65 |
| | CV % | 12.9 | 25.0 | 95.6 |
| | Min | 0.25 h (15 min) | 0.17 h (10.2 min) | 0.25 h (15 min) |
| | Max | 0.33 h (19.8 min) | 0.33 h (19.8 min) | 2.00 h (120 min) |

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating migraine associated with phonophobia or photophobia in a human patient in need thereof comprising:

a) providing a liquid formulation comprising 25 mg. or 50 mg. of diclofenac or a pharmaceutically acceptable salt thereof, wherein said formulation:
        i) is provided as a powder formulation and dissolved or suspended in water immediately before administration, or as a liquid formulation that is ingested with or without further mixing;
        ii) optionally has been shown to achieve a $C_{max}$ of from about 1500 to about 2500 ng/ml; and
        iii) has been shown to achieve $t_{max}$ in from about 10 to about 25 minutes; and
    b) orally administering said formulation to a patient suffering from migraine associated with photophobia or phonophobia.

2. The method of claim 1 further comprising diagnosing said patient suffering from migraine as requiring sustained migraine relief for at least 24 hours.

3. The method of claim 1 wherein said liquid formulation comprises about 50 mg. of diclofenac potassium.

4. The method of claim 1 wherein said formulation has been shown to achieve $t_{max}$ in from about 10 to about 20 minutes.

5. The method of claim 4 wherein said formulation has been shown to achieve a $C_{max}$ of from about 1400 to about 2500 ng/ml.

6. The method of claim 4 wherein said formulation has been shown to achieve a $C_{max}$ of from about 1500 to about 2500 ng/ml.

7. The method of claim 1 wherein said formulation has been shown to achieve a $C_{max}$ of from about 1500 to about 2500 ng/ml.

8. The method of claim 1 wherein said formulation has been shown to achieve a $C_{max}$ of from about 1400 to about 2500 ng/ml.

9. The method of claim 4 wherein said formulation comprises approximately 25 mg. of diclofenac or a pharmaceutically acceptable salt thereof, and said formulation has been shown to achieve a $C_{max}$ of from about 850 to about 1150 ng/ml.

10. A method of treating recurrent migraine in a human patient in need thereof suffering from migraine comprising:
  a) providing a liquid formulation comprising about 25 mg. or 50 mg. of diclofenac or a pharmaceutically acceptable salt thereof, wherein said formulation:
    i) is provided as a powder formulation and dissolved or suspended in water immediately before administration, or as a liquid formulation that is ingested with or without further mixing;
    ii) optionally has been shown to achieve a $C_{max}$ of from about 1500 to about 2500 ng/ml; and
    iii) has been shown to achieve $t_{tmax}$ in from about 10 to about 25 minutes; and
  b) diagnosing a patient suffering from migraine as requiring sustained migraine relief for at least 24 hours; and
  c) orally administering said formulation to said patient.

11. The method of claim 10 wherein said patient suffers from headache pain and either photophobia or phonophobia or both.

12. The method of claim 10 wherein said liquid formulation comprises about 50 mg. of diclofenac potassium.

13. The method of claim 10 wherein said $C_{max}$ has an inter-subject variability of less than about 70%.

14. The method of claim 10 wherein said $t_{max}$ has an inter-subject variability of less than about 70%.

15. The method of claim 10 wherein said formulation has been shown to achieve $t_{max}$ in from about 10 to about 20 minutes.

16. The method of claim 10 wherein said formulation has been shown to achieve a $C_{max}$ of from about 1400 to about 2500 ng/ml.

17. The method of claim 10 wherein said formulation has been shown to achieve a $C_{max}$ of from about 1500 to about 2500 ng/ml.

18. The method of claim 15 wherein said formulation has been shown to achieve a $C_{max}$ of from about 1400 to about 2500 ng/ml.

19. The method of claim 15 wherein said formulation has been shown to achieve a $C_{max}$ of from about 1500 to about 2500 ng/ml.

20. The method of claim 15 wherein said formulation comprises approximately 25 mg. of diclofenac or a pharmaceutically acceptable salt thereof, and said formulation has been shown to achieve a $C_{max}$ of from about 850 to about 1150 ng/ml.

21. A method of treating migraine in a human patient in need thereof comprising:
  a) providing a liquid formulation comprising about 25 mg. or 50 mg. of diclofenac or a pharmaceutically acceptable salt thereof, wherein said formulation:
    i) is provided as a powder formulation and dissolved or suspended in water immediately before administration, or as a liquid formulation that is ingested with or without further mixing;
    ii) optionally has been shown to achieve a $C_{max}$ of from about 1500 to about 2500 ng/ml; and
    iii) has been shown to achieve $t_{max}$ in from about 10 to about 20 minutes; and
  b) orally administering said formulation to a patient suffering from migraine, wherein said migraine is defined as a disease manifested in a population of patients by periodic attacks of headache pain, nausea, photophobia and phonophobia.

22. The method of claim 21 wherein said patient suffers from headache pain and either photophobia or phonophobia or both.

23. The method of claim 21 further comprising diagnosing said patient suffering from migraine as requiring sustained migraine relief for at least 24 hours.

24. The method of claim 21 wherein said $C_{max}$ has an inter-subject variability of less than about 70%.

25. The method of claim 21 wherein said $t_{max}$ has an inter-subject variability of less than about 70%.

26. The method of claim 21 wherein said liquid formulation comprises about 50 mg. of diclofenac potassium.

27. The method of claim 21 wherein said formulation has been shown to achieve $t_{max}$ in from about 10 to about 20 minutes.

28. The method of claim 21 wherein said formulation has been shown to achieve a $C_{max}$ of from about 1400 to about 2500 ng/ml.

29. The method of claim 21 wherein said formulation has been shown to achieve a $C_{max}$ of from about 1500 to about 2500 ng/ml.

30. The method of claim 27 wherein said formulation has been shown to achieve a $C_{max}$ of from about 1400 to about 2500 ng/ml.

31. The method of claim 27 wherein said formulation has been shown to achieve a $C_{max}$ of from about 1500 to about 2500 ng/ml.

32. The method of claim 27 wherein said formulation comprises approximately 25 mg. of diclofenac or a pharmaceutically acceptable salt thereof, and said formulation has been shown to achieve a $C_{max}$ of from about 850 to about 1150 ng/ml.

33. A method of treating acute pain in a human patient in need thereof for at least eight hours, comprising:
  a) providing an oral formulation comprising about 25 mg. or 50 mg. of diclofenac or a pharmaceutically acceptable salt thereof, wherein said formulation:
    i) optionally has been shown to achieve a $C_{max}$ of from about 1400 to about 2500 ng/ml; and
    ii) has been shown to achieve $t_{max}$ in from about 10 to about 35 minutes; and
  b) orally administering said formulation to a patient suffering from acute pain, no more than 3 total times in a 24 hour period;
  thereby providing pain relief to said patient for at least eight hours.

34. The method of claim 33 wherein said formulation has been shown to achieve $t_{max}$ in from about 10 to about 30 minutes.

35. The method of claim 33 wherein said acute pain is post-operative dental pain.

36. The method of claim 33 wherein said formulation has been shown to achieve a $C_{max}$ of from about 1500 to about 2500 ng/ml.

37. The method of claim 33 wherein said formulation has been shown to achieve a $C_{max}$ of from about 1400 to about 2500 ng/ml.

38. The method of claim 34 wherein said formulation has been shown to achieve a $C_{max}$ of from about 1400 to about 2500 ng/ml.

39. The method of claim 34 wherein said formulation has been shown to achieve a $C_{max}$ of from about 1500 to about 2500 ng/ml.

40. The method of claim 34 wherein said formulation comprises approximately 25 mg. of diclofenac or a pharmaceutically acceptable salt thereof, and said formulation has been shown to achieve a $C_{max}$ of from about 850 to about 1150 ng/ml.

* * * * *